United States Patent
Biagini et al.

(10) Patent No.: US 7,273,913 B2
(45) Date of Patent: Sep. 25, 2007

(54) PROCESS FOR THE PREPARATION OF ETHYLENE COPOLYMERS

(75) Inventors: Paolo Biagini, Trecate-Novara (IT); Stefano Ramello, Novara (IT); Roberto Provera, Vercelli (IT); Roberto Santi, deceased, late of Novara (IT); by Maria Rivellini, legal representative, Novara (IT); by Stefano Santi, legal representative, Novara (IT); by Laura Santi, legal representative, Novara (IT)

(73) Assignee: Polimeri Europa S.p.A., Brindisi (IT)

( * ) Notice: Subject to any disclaimer, the term of this patent is extended or adjusted under 35 U.S.C. 154(b) by 0 days.

(21) Appl. No.: 10/496,461

(22) PCT Filed: Nov. 18, 2002

(86) PCT No.: PCT/EP02/10639
§ 371 (c)(1),
(2), (4) Date: Oct. 25, 2004

(87) PCT Pub. No.: WO03/045963
PCT Pub. Date: Jun. 5, 2003

(65) Prior Publication Data
US 2006/0014911 A1 Jan. 19, 2006

(30) Foreign Application Priority Data
Nov. 30, 2001 (IT) .......................... MI2001A2516

(51) Int. Cl.
*C08F 4/76* (2006.01)
(52) U.S. Cl. ....................... 526/170; 526/160; 526/943; 526/348
(58) Field of Classification Search ................ 526/170, 526/943, 941, 160
See application file for complete search history.

(56) References Cited
FOREIGN PATENT DOCUMENTS

| EP | 955 304 A2 | * 11/1999 |
| EP | 0955304 | 11/1999 |
| EP | 1013675 | 6/2000 |

* cited by examiner

*Primary Examiner*—Ling-Sui Choi
*Assistant Examiner*—Rip A. Lee
(74) *Attorney, Agent, or Firm*—Oblon, Spivak, McClelland, Maier & Neustadt, P.C.

(57) ABSTRACT

A process is described for the preparation of ethylene copolymers having a wide molecular weight distribution, characterized in that it is carried out in the presence of meso- and rac-stereoisomeric mixtures of metallocene compounds having general formula (I), wherein A' and A", the same or different, are a radical of the η?5⅄-tetrahydroindenyl type (Ia)

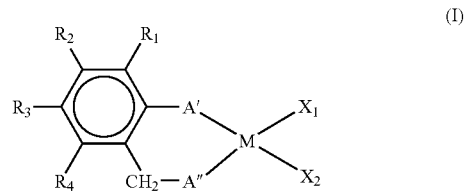

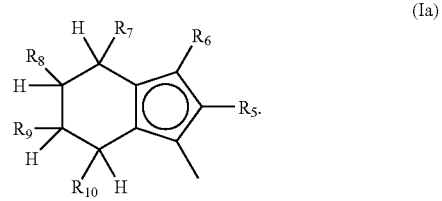

9 Claims, No Drawings

PROCESS FOR THE PREPARATION OF ETHYLENE COPOLYMERS

The present invention relates to a process for obtaining ethylene copolymers having a wide molecular weight distribution.

More specifically, the present invention relates to a process for obtaining ethylene/alpha-olefin copolymers characterized in that it is carried out in the presence of one or more metallocenes consisting of a racemic and meso mixture of stereoisomers.

There has recently been a great deal of development in the production of ethylene/alpha-olefin copolymers using catalysts based on metallocenes. Metallocenes, in fact, offer the advantage of having a greater catalytic activity than the traditional Ziegler-Natta catalysts and are described as "single-site" catalysts. Due to this "single-site" nature, the ethylene/alpha-olefins copolymers produced in the presence of metallocenes are usually uniform in their molecular structure. For example, with respect to the traditional copolymers obtained with Ziegler-Natta catalysts, copolymers from metallocenes have a relatively narrow molecular weight distribution (MWD).

Although certain properties of the copolymers from metallocenes are improved by narrow MWD, there are often difficulties in processing these materials to give end-products or films, with respect to the copolymers obtained with traditional Ziegler-Natta catalysts.

A possibility for overcoming this drawback consists in adding so-called "processing aids", i.e. substances suitable for improving the processability, to the copolymers. This requires additional processing and is therefore expensive.

Another approach consists in preparing compositions which are mixtures of different polymeric materials, with the aim of maximizing the best properties and contemporaneously minimizing processability problems. This requires a further operation with an increase in the cost of the materials produced. The following patents relate to this mixture technology: U.S. Pat. Nos. 4,598,128; 4,547,551; 5,408,004; 5,382,630; 5,382,631; 5,326,602; WO 94/22948 and WO 95/25141.

Another means of solving the problem of processability lies in the development of various cascade processes, in which the material is produced by a series of polymerizations under different conditions, for example in a series of reactors. In this way, a material is produced, which is very similar to a mixture and the copolymers can have an improved processability, but these methods are also costly and complicated with respect to the use of a single reactor.

Another potentially feasible solution for improving the processability consists in the use of multicomponent catalysts. In certain cases, in fact, a metallocene catalyst and a Ziegler-Natta catalyst supported on the same carrier or a catalyst consisting of two metallocenes, are used. In this way, components having a different molecular weight and composition are produced, in a single reactor and adopting a single set of polymerization conditions (see WO 95/11264 and EP 676,418). This approach however is difficult from the point of view of process control and preparation of the catalyst.

EP-A-955,304 describes a group of metallocene compounds with a bridged structure useful in the preparation of α-olefin (co) polymers.

It has now been found that it is possible to obtain ethylene copolymers having a wide molecular weight distribution using a single group of metallocenes selected from those described in the above patent application.

In accordance with this, the present invention relates to meso- and rac-stereoisomeric mixtures of metallocene compounds having general formula (I):

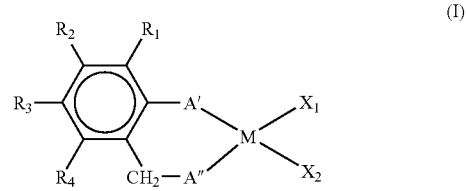

wherein
M is selected from titanium, zirconium, hafnium, preferably from zirconium and hafnium, even more preferably M=Zr;
$X_1$ and $X_2$, the same or different, are selected from halogen, amide, carboxy, alkoxy, carbamate, alkyl, aryl, hydrogen; they are preferably selected from halogen, $C_1$-$C_7$ hydrocarbyl radical, hydrogen, and are even more preferably chlorine;
A' and A", the same or different, are a radical of the $\eta^5$-tetrahydroindenyl type (Ia):

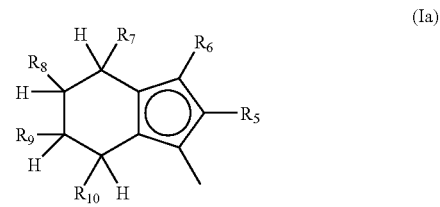

wherein the groups $R_5$, $R_6$, $R_7$, $R_8$, $R_9$, $R_{10}$, the same or different, are selected from hydrogen, a $C_1$-$C_8$ aliphatic radical, a $C_5$-$C_{12}$ cycloaliphatic radical, a $C_6$-$C_{14}$ aryl radical, preferably from hydrogen, methyl, ethyl, phenyl;
the groups $R_1$, $R_2$, $R_3$, $R_4$, the same or different, are selected from hydrogen, a $C_1$-$C_8$ aliphatic radical, a $C_5$-$C_{12}$ cycloaliphatic radical, a $C_6$-$C_{14}$ aryl radical, halogen, and are preferably hydrogen, methyl, benzyl, fluorine, even more preferably hydrogen.

Said stereoisomeric mixtures have a meso- content ranging from 20 to 80%, the complement to 100 consisting of rac-isomer.

In the preferred embodiment, the compound having general formula (I) consists of an about 50/50 mixture of the two meso- and rac-stereoisomers.

The compound having general formula (I) can be obtained by the selective reduction of $\eta^5$-1-indenyl complexes to give the $\eta^5$-1-tetrahydroindenyl complexes of the present invention, preferably with hydrogen in the presence of platinum oxide.

The reaction between anions of cyclopentadienyl, indenyl or fluorenyl ligands and salts of transition metals, can generally produce achiral metallocenes or metallocenes having various types of stereoisomerism in relation to the symmetry of the ligands with which the reaction is effected. In particular, ligands of the bridged bis-indenyl type, with the bridge bound in positions 1 and 1', respectively, when used in the formation of metallocenes of Group 4, can cause the formation of rac- and meso-bis (indenyl) metal dichlorides, as the π sides of each 1-substituted indenyl ligand are enantiotopic. In this document, the planar chirality of the complexes described refers to the definition of R. L. Halterman contained in "Metallocenes synthesis reactivity applications" A. Togni and R. L. Halterman editors, Wiley- VCH, Weinheim (1998), volume 1, pages 456-469. According to this definition, the R or S planar chirality is assigned on the basis of the configuration, according to Cahn-Ingold-Prelog, of the carbon atom in position 1 of the ligand and considering the metal as individually bound to all five carbon atoms of the cyclopentadienyl ring. In this way, the chirality can be described as (p-R) or (p-S) or (1R) or (1S), to emphasize that this definition of planar chirality is based on position 1 of the ligand. For greater clarity, the concepts described above are illustrated in Scheme 1, which shows the various possibilities of obtaining bridged bis-tetrahydroindenyl complexes with an o-benzylidene group bound in positions 1 and 1'.

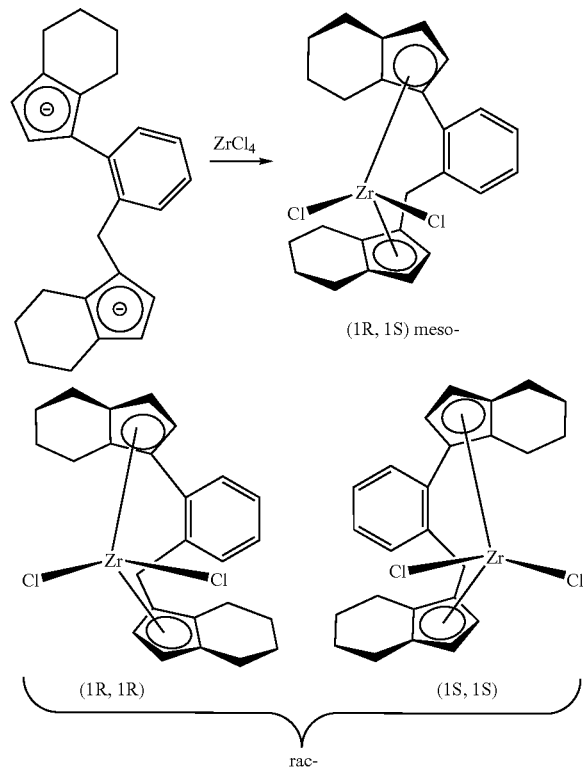

Scheme 1: Possibility of forming meso- and rac-complexes by the reaction of $ZrCl_4$ with dianions of bis-tetrahydroindenyl ligands bridged in position 1, 1'.

The present invention also relates to a process for the preparation of ethylene copolymers having a wide molecular weight distribution, characterized in that it is carried out in the presence of a meso- and rac-stereoisomeric mixture of metallocene compounds having general formula (I):

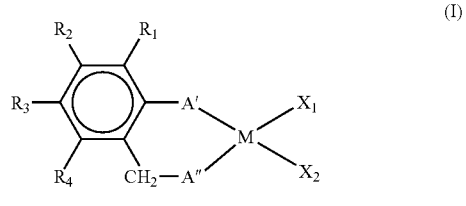

wherein
M is selected from titanium, zirconium, hafnium, preferably from zirconium and hafnium;
$X_1$ and $X_2$, the same or different, are selected from halogen, amide, carboxy, alkoxy, carbamate, alkyl, aryl, hydrogen; they are preferably selected from halogen, $C_1$-$C_7$ hydrocarbyl radical, hydrogen, and are even more preferably chlorine;
A' and A", the same or different, are a radical of the $\eta^5$-tetrahydroindenyl type (Ia):

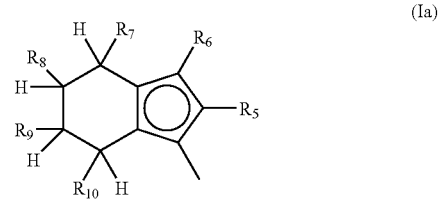

wherein the groups $R_5$; $R_6$, $R_7$, $R_8$, $R_9$, $R_{10}$, the same or different, are selected from hydrogen, a $C_1$-$C_8$ aliphatic radical, a $C_5$-$C_{12}$ cycloaliphatic radical, a $C_6$-$C_{14}$ aryl radical, preferably from hydrogen, methyl, ethyl, phenyl;
the groups $R_1$, $R_2$, $R_3$, $R_4$, the same or different, are selected from hydrogen, a $C_1$-$C_8$ aliphatic radical, a $C_5$-$C_{12}$ cycloaliphatic radical, a $C_6$-$C_{14}$ aryl radical, halogen, and are preferably hydrogen, methyl, benzyl, fluorine, even more preferably hydrogen.
In the preferred embodiment:

$R_1=R_2=R_3=R_4=R_5=R_6=R_7=R_8=R_9=R_{10}=H$;
M=Zr.

Typical examples of metallocenes, consisting of meso- and rac-stereoisomeric mixtures, having general formula (I), which can be used for the production of ethylene copolymers according to the present invention are:
o-benzylidenebis-($\eta^5$-1-tetrahydroindenyl)zirconium dichloride;
o-benzylidenebis-($\eta^5$-1-tetrahydroindenyl)zirconium dimethyl;
o-benzylidenebis-($\eta^5$-1-tetrahydroindenyl)zirconium diacetate;
o-benzylidenebis-($\eta^5$-1-tetrahydroindenyl)zirconium dimethoxide;
o-benzylidenebis-($\eta^5$-1-tetrahydroindenyl)zirconium dihydride;
o-benzylidenebis-($\eta^5$-1-tetrahydroindenyl) zirconium dibenzyl;
o-benzylidenebis-($\eta^5$-1-tetrahydro-3-methylindenyl)zirconium dichloride;
o-benzylidenebis-($\eta^5$-1-tetrahydro-3-phenylindenyl)zirconium dichloride;
o-benzylidenebis-($\eta^5$-1-tetrahydroindenyl)titanium dichloride;
o-benzylidenebis-($\eta^5$-1-tetrahydroindenyl)titanium dimethyl;
o-benzylidenebis-($\eta^5$-1-tetrahydroindenyl)hafnium dichloride;
o-benzylidenebis-($\eta^5$-1-tetrahydro-3-methylindenyl) hafnium dichloride;
o-benzylidenebis-($\eta^5$-1-tetrahydro-3-phenylindenyl) hafnium dichloride;
o-benzylidene-3-methylbis-($\eta^5$-1-tetrahydroindenyl)zirconium dichloride;

o-benzylidene-3-phenylbis-($\eta^5$-1-tetrahydroindenyl)zirconium dichloride;

o-benzylidene-3-methylbis-($\eta^5$-1-tetrahydroindenyl)zirconium dimethyl.

The catalytic system used in the present invention also comprises, in addition to a meso- and rac-stereoisomeric mi1ture of a metallocene having general formula (I), another component (which we will call cocatalyst) selected from an alumoxane and compounds having general formula (V) $(Ra)_xNH_{4-x}B(Rd)_4$ (wherein x is selected from 1, 2 or 3) or (VI) $(Ra)_3PHB(Rd)_4$, or (VII) $B(Rd)_3$, or (VIII) $(C_6H_5)_3CB(Rd)_4$, which, by reaction with a metallocene having general formula (I), are capable of generating catalytic systems of an ionic nature. In the above compounds having general formula (V), (VI), (VII) or (VIII), the Ra groups, the same or different, are monofunctional alkyl or aryl radicals, whereas Rd, the same or different, are monofunctional aryl radicals, preferably partially or totally fluorinated, even more preferably totally fluorinated.

As is known, the nature of the cocatalyst determines the preparation procedure of the catalytic system. A general description follows of two preparative methods of the catalytic system, both well known to experts in the field.

According to a first method, the catalytic system is prepared starting from one or more metallocenes having general formula (I) and an alumoxane. The general term alumoxane indicates an aluminum compound which can have a linear or cyclic structure. The linear structure has general formula (IX) $(R_e)_2$—Al—O—[—Al—$(R_e)$—O—]$_p$—Al$(R_e)_2$, whereas in its cyclic form it has general formula (X) —[—O—Al$(R_e)$—O—]$_{p+2}$— wherein the various $R_e$, the same or different, are selected from H, $C_1$-$C_6$ alkyl radicals, $C_6$-$C_{18}$ aryl radicals; "p" is an integer from 2 to 50, preferably from 10 to 35. If the various $R_e$ are the same, they are selected from methyl, ethyl, propyl, isobutyl, and are preferably methyl.

If the various $R_e$ are different, they are preferably methyl and hydrogen or alternatively methyl and isobutyl, hydrogen and isobutyl being preferred.

The alumoxane can be prepared according to various methods known to experts in the field. One of the methods comprises, for example, the reaction of an aluminum alkyl and/or an alkylaluminum hydride with water (gaseous, solid, liquid or bound, such as crystallization water, for example) in an inert solvent, for example toluene. For the preparation of an alumoxane having different $R_e$ alkyl groups, two different aluminumtrialkyls (AlR$_3$+AlR'$_3$) are reacted with water (see S. Pasynkiewicz, Polyhedron 9 (1990) 429-430 and EP-A-302,424).

The exact nature of the alumoxane is not known; however toluene solutions of methyl-alumoxane are commercially available, such as the product Eurecene 5100 10T of Witco whose concentration in active aluminum is provided, thus considerably facilitating its use.

The catalytic system is prepared by adding a hydrocarbon solution at 10% by weight of alumoxane to the mixture of anhydrified monomers, previously charged into the polymerization reactor. The mixture is brought to the desired temperature and one or metallocenes selected from those having general formula (I), are then added, in such a quantity as to obtain a total concentration ranging from $10^{-8}$ to $10^{-4}$ molar (depending on its activity), and with a molar ratio aluminum/metallocene ranging from $2\times10^2$ to $2\times10^4$. In this way, the catalytic system is defined as being "prepared in situ".

Alternatively, the metallocene, or mixture of metallocenes, can be pre-activated with the alumoxane before its use in the polymerization phase. In this case, one or more metallocenes having general formula (I) are dissolved in an inert hydrocarbon solvent, preferably aliphatic or aromatic, even more preferably toluene, so that the total concentration ranges from $10^{-1}$ to $10^{-4}$ molar. The toluene solution of alumoxane is then added so that the molar ratio aluminum/metallocene ranges from $2\times10^2$ to $2\times10^4$. The components are left to react for a time ranging from a few minutes to 60 hours, preferably from 5 to 60 minutes, at a temperature ranging from −78° C. to +100° C., preferably from 0° C. to 70° C. This preparation procedure of the catalytic system is commonly defined as "pre formation". At the end of the pre formation time, the mixture containing the catalytic system is added to the mixture of monomers previously prepared in the polymerization reactor, so that the final concentration of the metallocene in the reactor ranges from $10^{-8}$ to $10^{-4}$ moles/liter.

According to a second method, the catalytic system is prepared again starting from one or more metallocenes having general formula (I) and a cocatalyst having general formula (V), (VI), (VII) or (VIII). The operating procedure depends, in this case, on the nature of the X groups bound to M in general formula (I).

When X is equal to H or an alkyl radical, the catalytic system is prepared by adding one or more metallocenes having general formula (I) to the mixture of monomers previously prepared so that the total concentration ranges from $10^{-8}$ to $10^{-4}$ moles/liter. The mixture is brought to the desired temperature and a compound is added as cocatalyst, selected from those having general formula (V), (VI), (VII) or (VIII) as described in EP-A-277,004, in such a concentration that the total molar ratio cocatalyst/metallocene ranges from 0.1 to 10, preferably from 1 to 3.

When X is different to H or a hydrocarbyl radical, the catalytic system consists of one or more metallocenes having general formula (I), an alkylating compound selected from aluminum trialkyl, magnesium dialkyl and lithium alkyl, or other alkylating agents well known to experts in the field, and any one of the compounds having general formula (V), (VI), (VII) or (VIII) or one of their mixtures, as described in EP-A-612,769. The formation procedure of the catalytic system comprises premixing of the metallocene compound having general formula (I) with a suitable alkylating agent in aliphatic or aromatic hydrocarbon solvents, or their mixtures, at a temperature ranging from −20 to +100° C., preferably from 0° C. to 60° C. and even more preferably from +20° C. to +50° C., for a time varying from 1 minute to 24 hours, preferably from 2 minutes to 12 hours, even more preferably from 5 minutes to 2 hours.

The molar ratio between the alkylating compound and the compound having general formula (I) can vary from 1 to 1000, preferably from 10 to 500, even more preferably from 30 to 300.

The mixture is then put in contact with a compound having general formula (V), (VI), (VII) or (VIII) at the temperature specified above, for a time ranging from 1 minute to 2 hours, preferably from 2 minutes to 30 minutes, and is subsequently fed to the polymerization reactor. The molar ratio between the compound having general formula (V), (VI), (VII) or (VIII) and the metallocene (I) can vary from 0.1 to 10, preferably from 1 to 3.

Regardless of the method used for the preparation of the catalytic system, the reaction between the metallocene having general formula (I) and the cocatalyst can be carried out with or without varying quantities of one or all of the monomers to be polymerized. When small quantities of the monomers to be polymerized are present, i.e. with molar ratios monomer/metallocene ranging from 10 to 1000, what is defined in the known art as prepolymerization takes place, wherein small quantities of solid polymers are formed, which englobe almost all of the components of the catalytic system. This polymer/catalytic system suspension still shows a high catalytic activity and can be used to polymerize high quantities of monomers with an improvement in the morphological characteristics of the polymer obtained.

The catalytic systems of the present invention are generally used in very low molar concentrations, ranging from $10^{-8}$ to $10^{-4}$, expressed in metallocene having general formula (I). Although extremely diluted, these catalytic systems are characterized by a very high activity, ranging from 500 to 10000 Kg of polymer per gram of transition metal per hour of copolymerization. To obtain these activities at the above concentrations, however, the catalytic system must be carefully protected from poisons which are possibly present, also in parts per million, in the monomers, above all propylene, and in the solvents used in the polymerization reaction. This result can be obtained by the use, in the polymerization environment, of substances which are particularly effective in eliminating impurities characterized by the presence of active hydrogens, such as aluminum trialkyls, in particular aluminum trimethyl, aluminum triethyl, aluminum triisobutyl and aluminum diisobutylmonohydride. These substances do not directly take part in the catalytic process but are capable of effectively capturing the above poisons if used in concentrations of about $10^{-3}$-$10^{-4}$ molar in the polymerization environment.

Molecular weight control agents can be used in a combination with the above cocatalysts. Examples of these molecular weight control agents comprise hydrogen, aluminum hydride compounds, alkyl compounds of zinc and other known chain transfer agents.

The catalytic system of the present invention can be used in any known polymerization process (for example gas phase, solution, slurry) of monomers polymerizable by addition, comprising ethylenically unsaturated monomers, acetylene compounds, conjugated or non-conjugated dienes, polyenes and relative mixtures. Preferred monomers include olefins, for example α-olefins having from 2 to 30 carbon atoms, preferably from 2 to 8 carbon atoms, and relative combinations of two or more of these α-olefins. Examples of particularly convenient α-olefins are ethylene, propylene, 1-butene, 1-pentene, 4-methyl-1-pentene, 1-hexene, 1-heptene, 1-octene, 1-nonene, 1-decene, 1-undecene, 1-dodecene, 1-tridecene, 1-tetradecene and relative mixtures, as well as vinyl-terminated oligomeric chains or polymeric reaction products formed during the polymerization. The α-olefins are preferably ethylene, propene, 1-butene, 4-methyl-1-pentene, 1-hexene, 1-octene and combinations of ethylene and/or propene with one or more other α-olefins, and are even more preferably ethylene, propene, 1-butene, 1-hexene, 1-octene and relative combinations of two or more of these.

The polymerization is generally carried out under conditions well known in literature for polymerization reactions of the Ziegler-Natta or Kaminsky-Sinn type. The polymerization can be carried out in suspension, in solution, in slurry or in gas phase, batchwise or in continuous.

Examples of these well known polymerization processes are provided in WO 88/02009, U.S. Pat. Nos. 5,084,534; 5,405,922; 4,588,790; 5,032,652. The preferred polymerization temperatures range from 0 to 250° C., whereas the preferred polymerization pressures range from atmospheric pressure to 3000 atmospheres.

The process of the present invention is preferably carried out in a single reactor.

In most polymerization reactions, the molar ratio catalyst/polymerizable compounds ranges from $10^{-12}$:1 to $10^{-1}$:1, more preferably $10^{-5}$:1.

In the case of polymerization in solution and/or suspension, convenient solvents, consisting of inert liquids, comprise linear and branched hydrocarbons such as, for example, propane, butane, isobutane, pentane, hexane, heptane, octane, iso-octane, and relative mixtures; cyclic hydrocarbons, also variably alkyl substituted, such as cyclohexane, cycloheptane, methylcyclohexane, methylcyclopentane and relative mixtures; perfluorinated hydrocarbons such as $C_4$-$C_{10}$ perfluorinated alkanes; aromatic hydrocarbons and alkylsubstituted aromatic hydrocarbons such as benzene, toluene, xylene and relative mixtures. Convenient solvents are also those which comprise liquid olefins that can also act as monomers or comonomers, such as propylene, 1-butene, butadiene, cyclopentene, 1-hexene, 1-heptene, 3-methyl-1-pentene, 4-methyl-1-pentene, 1,4-hexadiene, 1,7-octadiene, 1,9-decadiene, 1-octene, 1-decene, styrene, divinylbenzene, ethylidene-norbornene, allylbenzene, vinyltoluene, 4-vinylcyclohexene, vinylcyclohexane, and relative mixtures.

One of these polymerization processes comprises putting one or more α-olefins in contact, optionally in a solvent, with a catalyst in one or more reactors in continuous of the stirred or tubular-type, see for example U.S. Pat. Nos. 5,272,236 and 5,278,272.

The process of the present invention can also be advantageously used in the (co)polymerization in gas phase of olefins. Polymerization processes of olefins in gas phase are well known in literature, and in particular the homopolymerization and copolymerization of ethylene and propylene, and the copolymerization of ethylene with higher α-olefins, such as 1-butene, 1-hexene, 4-methyl-1-pentene. The above processes are commercially used on a wide scale for the production of high density polyethylene (HDPE), medium density polyethylene (MDPE), linear low density polyethylene (LLDPE) and polypropylene.

The process in gas phase used can be, for example, of the type adopting, as polymerization reaction zone, a mechanically stirred bed or a gas fluidized bed. A large number of patents describe processes in gas phase, see, for example, U.S. Pat. Nos. 4,588,790; 4,543,399; 5,352,749; EP-A-659,773; EP-A-692,500; WO 94/29032; WO 94/25497.

The ethylene copolymers obtained with the process of the present invention have the characteristic of having a quantity of comonomer of over 50% (with respect to the total content present) concentrated at 50% by weight of the fractions with a higher molecular weight than the copolymer itself.

The following examples are provided for a better understanding of the present invention.

EXAMPLES

The analytical techniques and characterization methods listed and briefly described below were used in the following examples.

The characterization by $^1$H-NMR and $^{13}$C-NMR spectroscopy, mentioned in the following examples, was effected on a nuclear magnetic resonance spectrometer mod. Bruker AM-300.

The characterization of the complexes, by means of mass spectrometry, was effected using a Finnigan Mat 8400 double focus, inverse geometry, spectrometer.

The molecular weight measurement of the olefinic polymers was carried out by means of Gel-Permeation chromatography (GPC). The analyses of the samples were effected in 1,2,4-trichloro-benzene (stabilized with Santonox) at 135° C. with a WATERS 150-CV chromatograph using a Waters differential refractometer as detector.

The chromatographic separation was obtained with a set of μ-Styragel HT columns (Waters) of which three with pore dimensions of $10^3$, $10^4$, $10^5$ Å, and two with pore dimensions of $10^6$ Å, establishing a flow-rate of the eluant of 1 ml/min.

The data values were acquired and processed by means of Maxima 820 software version 3.30 (Millipores); the number average molecular weight (Mn) and weight average molecular weight (Mw) calculation was effected by means of universal calibration, selecting polystyrene standards with molecular weights within the range of 6,500,000-2,000, for the calibration.

The content of units deriving from 1-hexene or 1-octene in the polymers was determined by means of the known techniques based on $^{13}$C-NMR spectroscopy.

The commercial reagents listed below were used in the preparations described in the examples:

| | | |
|---|---|---|
| *** | n-butyl-lithium (LiBu) 1.6 M in hexane | ALDRICH |
| *** | zirconium tetrachloride (ZrCl$_4$) | FLUKA |
| *** | methylalumoxane (MAO) (Eurecene 5100 10T, 10% weight/volume of Al in toluene) | WITCO |
| *** | platinum dioxide (PtO$_2$) | ALDRICH |
| *** | molecular sieves (3A) | ALDRICH |

The reagents and/or solvents used and not indicated above are those commonly adopted in laboratories and on an industrial scale and can be easily found at the usual commercial operators specialized in the field.

Example 1

Synthesis of o-benzylidenebis-($\eta^5$-1-indenyl)-zirconium dichloride (III).

The procedure described herein has a few variations with respect to that provided in EP-A-955,304.

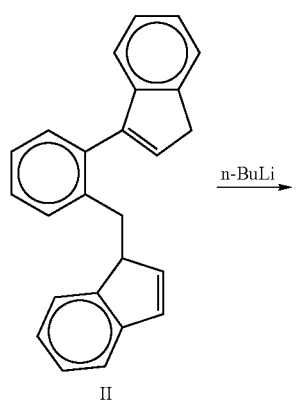

II

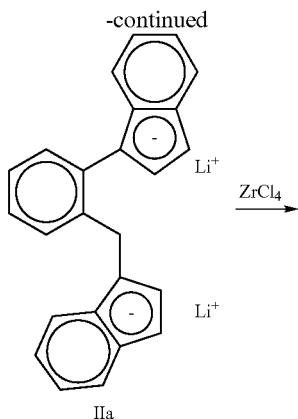

IIa

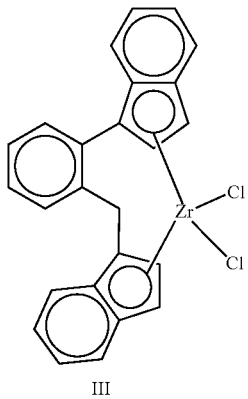

III 4.51 g of ligand having formula (II) (14.1 mmoles), obtained as described in EP-A-955,304, and 100 ml of anhydrous ethyl ether are charged, under an atmosphere of argon, into a 250 ml tailed test-tube, equipped with a magnetic stirrer. 21 ml of LiBu (1.6 M in hexane) (33.6 mmoles) are added dropwise, at room temperature, to the pale yellow solution thus obtained and the mixture is kept under stirring for about 12 h. At the end, the volume of the reaction mixture is reduced to about 20 ml, most of the solvent being removed at reduced pressure, and 50 ml of anhydrous n-hexane are then added. A suspension is immediately formed, which is filtered; the solid is collected and subsequently washed with n-hexane (3×10 ml). It is dried under vacuum (about 10 Pa) and the dilithium derivative having formula (IIa) thus obtained, is transferred, under an atmosphere of argon, to a 100 ml tailed test-tube containing 50 ml of anhydrous toluene. 4.03 g of ZrCl$_4$ (17.3 mmoles) are added to the suspension thus obtained and the reaction mixture is then left under stirring at room temperature for about 16 h, after which it is filtered on a porous septum and the mother liquor containing the desired product is collected. The residue is washed again with toluene (3×10 ml) and the washing water is joined to the mother liquor. The toluene solution thus obtained is dried, eliminating the solvent at reduced pressure, and the yellow solid obtained is further dried under vacuum (10 Pa) for 6 h. 4.83 g of o-benzylidenebis-($\eta^5$-1-indenyl)zirconium dichloride (III) are obtained (72% yield). NMR analysis reveals that there are two isomers (meso- and rac-) in the product, in a ratio of about 50/50.

$^1$H-NMR (CDCl$_3$, δ ppm rel. to TMS): rac-isomer: 4.42 (1H, d, J 17.07), 4.66 (1H, d, J 17.06), 5.69 (1H, d, J 3.45), 6.50 (1H, d, J 3.30), 6.52 (1H, d, J 3.49), 6.64(1H, d, J 3.49), 7.10-7.40 (8H, m), 7.40-7.70 (4H, m); meso-isomer: 4.58 (2H, s), 6.27 (1H, d, J 3.48), 6.68 (1H, d, J 2.96), 6.74 (1H, d, J 3.53), 6.82 (1H, d, J 3.45), 7.10-7.40 (m, 8H), 7.40-7.70 (4H, m).

DCI-MS: m/z 478 (negative ions, greatest intensity peak of the cluster).

Example 2

Synthesis of o-benzylidenebis-($\eta^5$-1-tetrahydroindenyl)zirconium dichloride (IV).

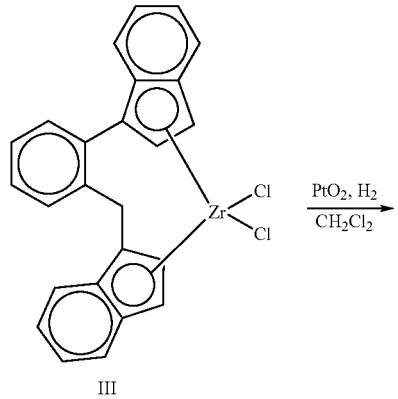

The following products are charged in order into an 80 ml steel autoclave: 1.17 g of o-benzylidenebis-($\eta^5$-1-indenyl) zirconium dichloride (III) (2.4 mmoles), 0.045 g of $PtO_2$ (0.2 nmoles), 1 g of molecular sieves (3A) and 30 ml of $CH_2Cl_2$. Hydrogen is then charged up to a pressure of 0.5 MPa, maintaining the apparatus at room temperature, and the mixture is left under stirring for about 3 h, care being taken to keep the hydrogen pressure constant. At the end, the suspension is filtered and the mother liquor recovered. The solvent is completely removed at reduced pressure and 30 ml of n-hexane are added to the residual solid; any possible insoluble products are removed by filtration, the solvent is then removed at reduced pressure and the extremely light-yellow residual solid is dried under vacuum (10 Pa) for 24 h. 0.73 g of o-benzylidenebis-($\eta^5$-1-tetrahydro-indenyl)-zirconium dichloride (IV) are thus obtained (yield 62%). NMR analysis reveals that there are two isomers (meso- and rac-) in the product, in a ratio of about 50/50.

$^1$H-NMR ($C_6DC_6$, δ ppm rel. to TMS): rac-isomer: 1.5-3.3 (16H, m), 3.84 (1H, d, J=17.26), 4.06 (1H, d, J=17.25), 5.37 (1H, d, J=3.14 Hz), 5.83 (1H, d, J=3.18 Hz), 6.09 (1H, d, J=3.13 Hz), 6.32 (1H, d, J=3.16 Hz), 7.30-7.41 (4H, m); meso-isomer: 1.5-3.3 (16H, m), 3.89 (2H, s), 5.62 (1H, d, J=3.30 Hz), 5.99 (1H, d, J=3.15 Hz), 6.13 (1H, d, J=3.24 Hz), 6.40 (1H, d, J=3.13 Hz), 7.20-7.40 (4H, m).

DCI-MS: m/z 486 (negative ions, greatest intensity peak of the cluster).

Example 3

Preparation of rac-o-benzylidenebis-($\eta^5$-1-indenyl) zirconium dichloride (IIIr) and meso-o-benzylidenebis-($\eta^5$-1-indenyl) zirconium dichloride (IIIm).

4.8 g of the complex (III) (10 mmoles) in which the two (meso- and rac-) isomers are present in a ratio of about 50/50, obtained as described in Example 1, and 20 ml of toluene, are charged, in an atmosphere of argon, into a 100 ml tailed test-tube, equipped with a magnetic stirrer. The suspension is filtered and the solid collected is dried under vacuum (about 10 Pa). 1.2 g of rac-o-benzylidenebis-($\eta^5$-1-indenyl) zirconium dichloride (IIIr) are thus obtained, having a stereoisomeric purity of 95%, determined by means of $^1$H-NMR.

The solvent is removed from the filtrate at reduced pressure and the residual solid is dried under vacuum (10 Pa). 3.6 g of meso-o-benzylidenebis-($\eta^5$-1-indenyl)zirconium dichloride (IIIm) are thus obtained, having a stereoisomeric purity of 67%, determined by means of $^1$H-NMR.

Example 4

Synthesis of rac-o-benzylidenebis-($\eta^5$-1-tetrahydroindenyl) zirconium dichloride (IVr).

The following products are charged in order into an 80 ml steel autoclave: 1.36 g of rac-o-benzylidenebis-($\eta^5$-1-indenyl)zirconium dichloride (IIIr) (2.9 mmoles), 0.047 g of $PtO_2$ (0.2 mmoles), 1 g of molecular sieves (3A) and 30 ml of $CH_2Cl_2$. Hydrogen is then charged up to a pressure of 0.5 MPa, maintaining the apparatus at room temperature, and the mixture is left under stirring for about 3 h, care being taken to keep the hydrogen pressure constant. At the end, the suspension is filtered and the mother liquor recovered. The solvent is completely removed at reduced pressure and 30 ml of n-hexane are added to the residual solid; any possible insoluble products are removed by filtration, the solvent is then removed at reduced pressure and the light-yellow residual solid is dried under vacuum (10 Pa) for 12 h. 0.96 g of rac-o-benzylidenebis-($\eta^5$-1-tetrahydro-indenyl)-zirconium dichloride (IVr) are thus obtained (yield 70%), having a stereoisomeric purity of 95%, determined by means of $^1$H-NMR.

$^1$H-NMR ($CDCl_3$, δ ppm rel. to TMS): 1.5-3.3 (16H, m), 3.84 (1H, d, J 17.26), 4.06 (1H, d, J 17.25), 5.37 (1H, d, J 3.14 Hz), 5.83 (1H, d, J 3.18 Hz), 6.09 (1H, d, J 3.13 Hz), 6.32 (1H, d, J 3.16 Hz), 7.30-7.41 (4H, m).

DCI-MS: m/z 486 (negative ions, greatest intensity peak of the cluster).

Example 5

Synthesis of meso-o-benzylidenebis-($\eta^5$-1-tetrahydro-indenyl)zirconium dichloride (IVm).

The following products are charged in order into an 80 ml steel autoclave: 1.36 g of meso-o-benzylidenebis-($\eta^5$-1-indenyl)zirconium dichloride (IIIm) (2.4 mmoles), 0.048 g of $PtO_2$ (0.2 mmoles), 1 g of molecular sieves (3A) and 30 ml of $CH_2Cl_2$. Following a procedure which is completely analogous to that described in Example 3, 0.83 g of meso-o-benzylidenebis-($\eta^5$-1-tetrahydro-indenyl)zirconium dichloride (IVm) are recovered at the end (yield 72%), having a stereoisomeric purity of 80%, determined by means of $^1$H-NMR.

$^1$H-NMR (CDCl$_3$, δ ppm rel. to TMS): 1.5-3.3 (16H, m), 3.89 (2H, s), 5.62 (1H, d, J=3.30 Hz), 5.99 (1H, d, J=3.15 Hz), 6.13 (1H, d, J=3.24 Hz), 6.40 (1H, d, J=3.13 Hz), 7.20-7.40 (4H, m).

DCI-MS: m/z 486 (negative ions, greatest intensity peak of the cluster).

Example 6 to 20

Copolymerization of ethylene/1-hexene (or 1-octene) using MAO as cocatalyst.

Examples 6 to 11 refer to a series of copolymerization tests for the preparation of modified polyethylenes based on ethylene/1-hexene, whereas Examples 17 to 20 refer to a series of copolymerization tests for the preparation of modified polyethylenes based on ethylene/1-octene, carried out using a catalytic system comprising the metallocene complex, obtained as described above in Example 2 and methylalumoxane (MAO) as cocatalyst. In Examples 12 to 16, a comparison is made in the production of ethylene/1-hexene copolymers using a catalytic system consisting of one of the metallocene complexes, prepared according to Examples 1, 3, 4 or 5 and MAO as cocatalyst. The specific polymerization conditions of each example and the results obtained are specified in Tables (I) and (II) below, which indicate in succession, the reference example number, the metallocene complex used, the quantity of zirconium used, the atomic ratio between the aluminum in the MAO and zirconium in the metallocene, the polymerization temperature, the concentration of comonomer (1-hexene or 1-octene) present in liquid phase expressed in molar percentage, the activity of the catalytic system expressed as kilograms of polymer per gram of metallic zirconium per hour: (kg$_{pol.}$/g$_{zr}$xh), the relative quantity, by weight, of the monomeric units (C$_6$ or C$_8$) in the polymer, the weight average molecular weight M$_w$ and M$_w$/M$_n$ molecular weight dispersion.

The polymerization is carried out in an 0.5 liter pressure reactor, equipped with a magnetic drag anchor stirrer and external jacket connected to a heat exchanger for the temperature control. The reactor is previously flushed by maintaining under vacuum (0.1 Pascal) at a temperature of 80° C. for at least 2 hours.

130 g of anhydrous n-heptane and the comonomer (1-hexene or 1-octene) are charged into the reactor, at 23° C., in such a quantity as to obtain the molar concentration indicated in the corresponding column in Tables (I) and (II) below. The reactor is then brought to the desired polymerization temperature (40-80° C.) and "polymerization grade" gaseous ethylene is fed by means of a plunged pipe until the desired total equilibrium pressure of 1.1 MPa is reached, as specified in Tables (I) and (II) below.

The MAO, as a 1.5 M solution (as Al) in toluene, and the desired quantity of one of the above metallocene complexes as a toluene solution having a concentration generally ranging from $3\times10^{-4}$ to $1\times10^{-3}$ M, are charged into a suitable tailed test-tube, maintained under nitrogen. The catalyst solution thus formed is kept at room temperature for a few minutes and is then transferred under a stream of inert gas to a metal container from which, due to an over-pressure of nitrogen, it enters the reactor.

The polymerization reaction is carried out at the desired temperature, care being taken to keep the total pressure constant by continuously feeding ethylene to compensate the part which has reacted in the meantime. After 30 minutes, the ethylene feeding is interrupted and the polymerization is stopped by the addition of 10 ml of ethyl alcohol. After opening the autoclave, its contents are poured into a suitable glass container, containing 500 ml of ethyl alcohol. The suspension obtained is kept under stirring for about 30 minutes, in order to obtain the complete coagulation of the polymeric material present in the reaction mixture. Finally, the polymer is recovered by decanting or by filtration, depending an the morphology obtained and, after washing with two 100 ml portions of ethyl alcohol, it is dried at 60° C., at a reduced pressure of 1000 Pa, for at least 8 hours, in order to completely eliminate any possible residual monomers. The solid thus obtained is weighed and the activity of the catalyst is calculated as described above. The content of the different 1-hexene or 1-octene monomeric units, depending on the cases, is measured on the dried and homogenized solid, by means of the known techniques based on $^{13}$C-NMR spectroscopy, together with the weight average (M$_w$) and number average (M$^n$) molecular weight. The overall results are indicated in Tables I and II.

TABLE I ehtylene/1-hexene copolymerization according to Examples 6 to 16[a]. Complex IV forms part of the present invention, the others being provided for comparative purposes.

| Ex. Nr. | Compl. | Zr (mol. × 10$^{-8}$) | Al/Zr moles/moles | T (C. °) | C$_6$ (feed) (% moles) | Activity kg$_{pol.}$/g$_{Zr}$ × h | C$_6$ (pol.) (% weight) | M$_w$ (×10$^3$) | M$_w$/M$_n$ |
|---|---|---|---|---|---|---|---|---|---|
| 6 | IV | 0.11 | 4060 | 80 | 6.6 | 3856 | 5.4 | 162 | 4.1 |
| 7 | IV | 0.46 | 3799 | 60 | 6.6 | 2412 | 6.0 | 263 | 3.9 |
| 8 | IV | 0.57 | 3776 | 40 | 6.6 | 544 | 7.3 | 463 | 3.9 |
| 9 | IV | 0.46 | 3799 | 60 | 6.6 | 2399 | 5.8 | 284 | 3.7 |
| 10 | IV | 0.46 | 3799 | 60 | 9.6 | 1152 | 7.7 | 207 | 3.9 |
| 11 | IV | 0.458 | 3799 | 60 | 12.4 | 484 | 8.9 | 153 | 4.3 |
| 12 | IIIm | 0.31 | 3742 | 80 | 6.6 | 2481 | 5.8 | 222 | 2.2 |
| 13 | IIIr | 0.15 | 4833 | 80 | 6.6 | 3114 | 6.0 | 181 | 2.3 |
| 14 | III | 0.19 | 4088 | 80 | 6.6 | 2815 | 5.8 | 211 | 2.4 |
| 15 | IVr | 0.18 | 5576 | 80 | 6.6 | 4318 | 6.9 | 175 | 1.9 |
| 16 | IVm | 0.23 | 5065 | 80 | 6.6 | 2064 | 3.1 | 94 | 2.2 |

[a]Each example was carried out at an ethylene pressure equal to 1.1 MPa and using n-heptane as solvent.

Comments on Table I

As can be seen from the data summarized in Table I, the use of o-benzylidenebis-($\eta^5$-1-tetrahydroindenyl)zirconium dichloride (IV), in the production of ethylene/1-hexene copolymers (Examples 6-11), allows products to be obtained, having molecular weight distribution ($M_w/M_n$) values ranging from 3.7 to 4.3. This in itself is already an advantage with respect to the use of the analogous derivative with non-hydrogenated indenyl ligands o-benzyli-denebis-($\eta^5$-1-indenyl)zirconium dichloride (III), but on analyzing the comparative examples (12-16) in more detail, other positive aspects emerge, associated with the use of the complex (IV). The meso- and rac-stereoisomers (IIIm and IIIr, respectively), obtained according to the procedure described in Example 3, of which the complex o-benzylidenebis-($\eta^5$-1-indenyl)zirconium dichloride (III) consists, have a very similar behaviour in the production of ethylene/1-hexene copolymers (Examples 12 and 13) with respect to the quantity of comonomer inserted and the weight average molecular weight value, even if, considering the catalytic activity, there is still a certain difference in favour of the rac-isomer. There is a radical and unexpected change in the case of the analogous meso- and rac-stereoisomers (IVm and IVr, respectively), obtained according to the procedure described in Examples 4 and 5, of which the complex o-benzylidenebis-($\eta^5$-1-tetrahydro-indenyl)zirconium dichloride (IV) consists. As can be clearly seen, in fact, from Examples 15 and 16, the stereoisomer IVr shows a greater catalytic activity, contemporaneously providing polymers with a higher content of comonomer and with much higher weight average molecular weight values, with respect to the IVm stereoisomer. The use of the complex o-benzylidenebis-($\eta^5$-1-tetrahydro-indenyl)zirconium dichloride (IV), prepared as described in Example 2, therefore makes it possible to obtain ethylene/1-hexene copolymers which are characterized, in addition to a wide molecular weight distribution, as already mentioned above, also by a heterogeneous distribution of the comonomer with respect to the molecular weight, most of the 1-hexene being concentrated in the polymer fractions with a higher molecular weight (Examples 6 -11). These characteristics give the copolymers thus obtained a considerably improved processability with respect to analogous products having the same content of comonomer, prepared with other catalytic systems. Furthermore, the use of the complex o-benzylidenebis-($\eta^5$-1-tetrahydro-indenyl)zirconium dichloride (IV) allows, under the same experimental conditions, catalytic activities to be obtained, which are about 30% higher with respect to the analogous complex with non-hydrogenated indenyl ligands (III), thus reducing the catalysis costs.

Comments on Table II

The data provided in Table II demonstrate that the general characteristics of the copolymers obtained with the complex o-benzylidenebis-($\eta^5$-1-tetrahydro-indenyl)zirconium dichloride (IV), widely illustrated above, also remain unaltered for the copolymerization of ethylene/1-octene. Also in this case, in fact, the copolymers described all have molecular weight distributions ($M_w/M_n$) higher than 3.9, regardless of the temperature at which they were obtained and the quantity of comonomer fed.

The invention claimed is:

1. A process for the preparation of ethylene copolymers having a $M_w/M_n$ ratio of at least about 3.7, wherein the process is carried out in the presence of meso- and rac-stereoisomeric mixtures of metallocene compounds having general formula (I):

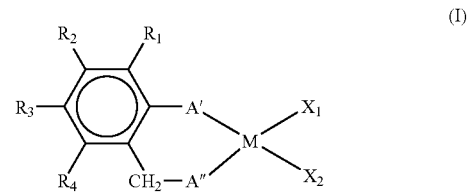

(I)

wherein
M is selected from the group consisting of titanium, zirconium, and hafnium; $X_1$ and $X_2$, the same or different, are selected from the group consisting of halogen, amide, carboxy, alkoxy, carbamate, alkyl, aryl, and hydrogen;
A' and A", the same or different, are a radical of the $\eta^5$-tetrahydroindenyl type(Ia):

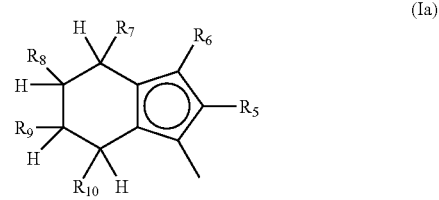

(Ia)

wherein the groups $R_5$, $R_6$, $R_7$, $R_8$, $R_9$, $R_{10}$, the same or different, are selected from the group consisting of hydrogen, a $C_1$-$C_8$ aliphatic radical, a $C_5$-$C_{12}$ cycloaliphatic radical, and a $C_6$-$C_{14}$ aryl radical; the groups $R_1$, $R_2$, $R_3$, $R_4$, the same or different, are selected from the group consisting of hydrogen, a $C_1$-$C_8$ aliphatic radical, a $C_5$-$C_{12}$ cycloaliphatic radical, a $C_6$-$C_{14}$ aryl radical, and halogen, wherein the

TABLE II ethylene/1-octene copolymerization according to Examples 17 to 20[a].

| Ex. Nr. | Compl. | Zr (mol. × $10^{-6}$) | Al/Zr moles/ moles | T (C. °) | $C_8$ (feed) (% moles) | Activity $kg_{pol.}/ g_{Zr} \times h$ | $C_8$ (pol.) (% weight) | $M_w$ (×$10^3$) | $M_w/M_n$ |
|---|---|---|---|---|---|---|---|---|---|
| 17 | IV | 0.46 | 3799 | 60 | 5.3 | 2172 | 8.9 | 248 | 3.9 |
| 18 | IV | 0.46 | 3799 | 60 | 10.2 | 1276 | 11.1 | 190 | 4.4 |
| 19 | IV | 0.18 | 3974 | 80 | 5.3 | 3011 | 6.1 | 155 | 4.5 |
| 20 | IV | 1.09 | 1593 | 80 | 10.2 | 1477 | 13.0 | 91 | 4.9 |

[a]Each example was carried out at an ethylene pressure equal to 1.1 MPa and using n-heptane as solvent.

stereoisomeric mixture has a content of meso-compound ranging from 20 to 80%, the complement to 100 consisting of rac-compound.

2. The process according to claim 1, wherein M is zirconium.

3. The process according to claim 1, wherein $X_1$ and $X_2$, the same or different, are selected from the group consisting of halogen, $C_1$-$C_7$ hydrocarbyl radical, and hydrogen.

4. The process according to claim 3, wherein $X_1$ and $X_2$ are chlorine.

5. The process according to claim 1, wherein $R_5$, $R_6$, $R_7$, $R_8$, $R_9$, $R_{10}$, the same or different, are selected from the group consisting of hydrogen, methyl, ethyl, and phenyl.

6. The process according to claim 1, wherein the groups $R_1$, $R_2$, $R_3$, $R_4$, the same or different, are selected from the group consisting of hydrogen, methyl, benzyl, and fluorine.

7. The process according to claim 6, wherein $R_1$=$R_2$=$R_3$=$R_4$=H.

8. The process according to claim 1, wherein the stereoisomeric mixture consists of a 50/50 mixture of the two meso- and rac-stereoisomers.

9. The process according to claim 1, wherein the $M_w/M_n$-ratio is at least about 3.9.

* * * * *